United States Patent [19]

Büssemeier et al.

[11] 4,423,156

[45] Dec. 27, 1983

[54] PROCESS FOR PREPARING UNSATURATED HYDROCARBONS

[75] Inventors: Bernd Büssemeier, Mulheim-Ruhr; Boy Cornils, Dinslaken; Carl-Dieter Frohning, Oberhausen, all of Fed. Rep. of Germany

[73] Assignee: Ruhrchemie Aktiengesellschaft, Oberhausen, Fed. Rep. of Germany

[21] Appl. No.: 502,536

[22] Filed: Jun. 13, 1983

Related U.S. Application Data

[63] Continuation of Ser. No. 299,746, Sep. 8, 1981, abandoned.

[30] Foreign Application Priority Data

Sep. 19, 1980 [DE] Fed. Rep. of Germany ....... 3035404

[51] Int. Cl.³ .......................... C07C 1/04; C07C 1/06
[52] U.S. Cl. ................................ 518/717; 518/715; 518/719; 518/721
[58] Field of Search ................ 518/715, 717, 719, 721

[56] References Cited

U.S. PATENT DOCUMENTS

2,167,004  7/1939  Pier et al. .
4,199,523  4/1980  Rottig .
4,261,865  4/1981  Hargis .
4,309,314  1/1982  Hargis et al. .

FOREIGN PATENT DOCUMENTS

2518964  11/1976  Fed. Rep. of Germany .

OTHER PUBLICATIONS

Storch et al., Fischer–Tropsch & Related Synthesis, John Wiley, New York, 1951, pp. 1–7.

*Primary Examiner*—Howard T. Mars
*Attorney, Agent, or Firm*—Jordan B. Bierman; Linda Bierman

[57] ABSTRACT

The conventional process for the preparation of unsaturated hydrocarbons comprises catalytic hydrogenation of carbon oxides at 220° to 500° C. and pressures of up to 30 bars. It has been found that, by carrying out the foregoing reaction in the presence of at least one low molecular weight aliphatic alcohol, the yield of olefins and the catalyst life are substantially and surprisingly improved.

9 Claims, No Drawings

PROCESS FOR PREPARING UNSATURATED HYDROCARBONS

This Application is a continuation of Ser. No. 299,746, filed Sept. 9, 1981 now abandoned which claims the priority of German P 30 35 404.2, filed Sept. 19, 1980.

The present invention relates to the preparation of short-chain olefins from synthesis gas.

In the hydrogenation of carbon oxides to olefins, the conversion depends to a great extent on the partial pressure of the hydrogen. The greater the hydrogen partial pressure, the greater will be the degree of conversion. However, at the same time, hydrogenation of the initially formed olefins also increases with increasing hydrogen partial pressure. In addition, the conversion of carbon monoxide by the water of reaction formed in the synthesis, according to:

$$H_2O + CO \rightleftharpoons H_2 + CO_2$$

should also be taken into account. This conversion occurs under the influence of the same catalysts which are used for the hydrogenation of the carbon oxides. In this way, a substantial proportion of the carbon monoxide used is lost. In practice, therefore, the object is to adjust the synthesis pressure and hydrogen partial pressure (in the presence of selectively acting catalysts) so that the hydrogenation of the carbon oxides will take place with a high degree of conversion, and the hydrogenation of the initially formed olefins, as well as the conversion reaction between carbon monoxide and water, will be largely suppressed.

The production of unsaturated—in particular gaseous—hydrocarbons by reacting carbon oxides with hydrogen in the presence of catalysts has already been described many times. Thus, for example, the process according to German Patent Specification No. 922 883 employs fused iron catalysts which are periodically or continuously removed from the reaction space, regenerated, reduced, and reused. The conversion is carried out at normal or slightly elevated pressure and at temperatures above about 450° C., preferably at 470° to 600° C.

According to another procedure, described in German Patent Specification No. 896,338, unsaturated gaseous hydrocarbons are obtained by reacting carbon monoxide with hydrogen in the presence of stable oxides of metals of Groups II to VII of the Periodic Table. The reaction is carried out at roughly atmospheric pressure and at temperatures above 520° C.

To produce ethylene by hydrogenating carbon monoxide with hydrogen, according to German Auslegeschrift No. 1 271 098, catalysts may also be used which consist of at least 98% by weight of a carrier and 0.3 to 2% by weight of cobalt, nickel or platinum. The conversion is carried out at a throughput rate of 2500 to 3000 liters of gas per liter of catalyst per hour at temperatures of 300° to 450° C. and pressures of 130 to 200 mm Hg. The process is characterized by good selectivity with regard to lower gaseous olefins although the achievable synthesis gas conversions (which are of the order of magnitude of 10 to 20%) are unsatisfactory.

A clear improvement in the degree of conversion of the starting substances and olefin yield is achieved with catalysts composed of iron and/or cobalt, together with titanium or thorium (cf. German Patent Specification No. 25 36 488).

According to German Patent Specification No. 25 18 964, unsaturated hydrocarbons, in particular gaseous olefins, can also be successfully produced in high yields and with high selectivity by using iron catalysts containing vanadium or manganese and also ZnO and $K_2O$.

The high reaction temperatures employed in the known processes result in the formation of carbon from carbon monoxide, in accordance with the Boudouard equilibrium. The deposition of carbon leads to deactivation because the catalyst surface becomes covered and, in individual cases, this causes the catalyst structure to "burst", the life of the catalyst thereby being considerably reduced.

A further disadvantage of the hitherto known processes for obtaining olefins from synthesis gas is the service life of the catalysts, which is not always satisfactory. It has been shown that often the selectivity with regard to olefin formation falls with increasing operating time, and the life of the catalysts is frequently reduced to a few hundred hours favored by high CO partial pressures and high reaction temperatures.

Therefore, there is a need for a process which overcomes the aforementioned disadvantages and insures the selective formation of olefins from synthesis gas with high degrees of conversion and yields, and a long active life of the catalysts.

According to the invention, unsaturated hydrocarbons, especially olefins with 2 to 4 carbon atoms, are obtained by catalytic hydrogenation of carbon oxides with hydrogen at 220° to 500° C. and pressures of up to 30 bars. The conversion is carried out in the presence of catalysts known per se with the addition of low molecular weight aliphatic alcohols to the carbon oxides/hydrogen mixture.

It has surprisingly been found that, according to the new process, the formation of short-chain olefins is synergistically enhanced by adding low-molecular weight alcohols to the synthesis gas. By using synthesis gas mixed with alcohols, the olefin yield is markedly higher than the sum of the amounts of olefins formed under the same reaction conditions with synthesis gas alone or with alcohols alone. Moreover, the effective life of the catalysts employed according to the invention is significantly raised.

The catalysts known per se and used within the scope of the new process may consist of iron as the essential component. Other metals of Group VIII of the Periodic Table, such as nickel, iridium, palladium or platinum, may also be used, although they are of less importance, since they lead to the formation of olefins only in minor amounts.

The catalysts may, in addition, contain activators which effect the formation of a large surface area and prevent recrystallization processes in the catalytically active phase. Besides, activators can influence the selectivity. As activators, mainly oxides of metals of Groups IIa and/or IIb of the Periodic System of the elements are used; especially MgO, CaO and ZnO, which are employed in an amount of 2 to 20% by weight (based on the weight of the catalyst). Alkali metal carbonates such as $NaCO_3$ or $K_2CO_3$ are also conventional activators. In order to improve the selectivity of the catalysts with respect to the formation of olefins with 2 to 4 carbon atoms, the addition of difficulty reducible oxides of vanadium and/or manganese in amounts of 5 to 50% by weight (based on the weight of the catalyst) as well as of titanium or thorium in amounts of 5 to 50% by weight (based on the catalyst weight) has proved very effective.

The catalysts are produced by precipitating the constituents from their aqueous solutions with suitable precipitation agents such as alkali metal carbonates. Another method of preparation is to mix and homogenize the constituents, and then shape and form the mass. Moreover, the catalysts may also be obtained by sintering the mixed components.

A low molecular weight aliphatic alcohols which, according to the process of the present invention, are passed over the catalyst together with the mixture of carbon oxides and hydrogen, those with 1 to 3 carbon atoms; i.e. methanol, ethanol, as well as the isomeric propanols, are considered to be particularly suitable. They may be used alone or as mixtures. The mixing ratio of carbon oxides and hydrogen to alcohol may be varied within wide limits. It has been found effective to use 1 to 4 parts by volume of the carbon oxides/hydrogen mixture to 1 part by volume of vapor state alcohol.

The expression "carbon oxides" is understood to mean carbon monoxide and carbon dioxide, or mixtures thereof. Synthesis gas, i.e. the mixture of carbon monoxide and hydrogen which can be obtained from low grade petroleum fractions, but in particular also from coal by partial oxidation in the presence of hydrogen according to known methods, is normally used as starting material for producing olefins according to the process of the invention.

In normal cases, the synthesis gas contains equal parts by volume of carbon monoxide and hydrogen. Mixtures rich in carbon oxides or hydrogen with carbon oxides to hydrogen proportions of 30:70 to 70:30 (in moles) may also be used.

The new process is easy to carry out and does not involve any special operational procedure. The catalysts are generally arranged in the form of a fixed bed. They may, however, also be employed according to other process variants; e.g. in finely divided form as a fluidised bed.

The starting substances, i.e. synthesis gas and alcohol, are led, at temperatures of 220° to 500° C., especially 250° to 350° C., and pressures of up to 30 bars, preferably 10 to 30 bars, over the catalyst. The gas mixture leaving the reaction space is conveniently fully or partially recycled, after removing the unsaturated gaseous hydrocarbons formed and replacing the alcohol consumed.

The invention is described in more detail with the aid of the following examples which are intended to illustrate, rather than limit, the invention.

All tests are carried out in a tubular reactor 150 cm long and 2 cm internal diameter. The reactor is filled with a mixture of 50 ml of catalyst and 250 ml of silicon carbide (SiC), which has good thermal conductivity. The height of the catalyst packing is 96 cm. After the reactor has been brought to the reaction temperature by means of electrical heating, the feedstock materials are led over the catalyst.

The catalysts used in the experiments have the following composition:

EXAMPLES 1 to 3

100 parts by weight of iron in the form of $Fe_2O_3$
80 parts by weight of vanadium in the form of $V_2O_5$
30 parts by weight of ZnO and 4 parts by weight of $K_2O$

EXAMPLE 4

100 parts by weight of iron in the form of $Fe_2O_3$
80 parts by weight of vanadium in the form of $V_2O_5$
7 parts by weight of MgO and 4 parts by weight of $K_2O$ The catalysts are produced by simple mixing and homogenization of the pulverulent constituents. The results are shown in the following Tables.

Example 1

| Feedstock | | Synthesis gas | Synthesis gas + methanol | Nitrogen + methanol |
|---|---|---|---|---|
| Catalyst | | ZnO—containing Fe—catalyst | | |
| Temperature | (°C.) | 335 | 335 | 330 |
| Pressure | (bars) | 10 | 10 | 10 |
| CO + $H_2$ feedstock | (V/Vh) | 1005 | 944 | — |
| $N_2$ feedstock | (V/Vh) | — | — | 980 |
| Alcohol (gas) feedstock | (V/Vh) | — | 562 | 591 |
| Yield | (g/$Nm^3$) | | | |
| Methane | (g/$Nm^3$) | 41.8 | 64.1 | 19.6 |
| Ethane | (g/$Nm^3$) | 24.7 | 25.5 | traces |
| Ethylene | (g/$Nm^3$) | 2.8 | 13.0 | " |
| Propane | (g/$Nm^3$) | 30.3 | 37.2 | " |
| Propylene | (g/$Nm^3$) | 22.7 | 39.0 | " |
| Butane | (g/$Nm^3$) | 8.8 | 8.7 | " |
| Butene | (g/$Nm^3$) | 15.2 | 24.8 | " |
| $C_2$-$C_4$ olefins | (g/$Nm^3$) | 40.7 | 76.8 | |

Example 2

| Feedstock | | Syntheses gas | Synthesis gas + ethanol | Nitrogen + ethanol |
|---|---|---|---|---|
| Catalyst | | ZnO—containing Fe—catalyst | | |
| Temperature | (°C.) | 330 | 330 | 330 |
| Pressure | (bars) | 10 | 10 | 10 |
| CO + $H_2$ feedstock | (V/Vh) | 839 | 920 | — |
| $N_2$ feedstock | (V/Vh) | — | — | 933 |
| Alcohol (gas) feedstock | (V/Vh) | — | 365 | 397 |
| Yield | (g/$Nm^3$) | | | |
| Methane | (g/$Nm^3$) | 14.6 | 11.5 | 0.7 |
| Ethane | (g/$Nm^3$) | 2.9 | 18.7 | 3.0 |
| Ethylene | (g/$Nm^3$) | 12.6 | 21.3 | 3.7 |
| Propane | (g/$Nm^3$) | 2.6 | 3.0 | 0.2 |
| Propylene | (g/$Nm^3$) | 18.8 | 28.7 | 0.9 |
| Butane | (g/$Nm^3$) | 1.7 | 1.6 | 0.2 |
| Butene | (g/$Nm^3$) | 13.1 | 24.7 | 5.6 |
| $C_2$-$C_4$ olefins | (g/$Nm^3$) | 44.5 | 74.7 | 10.2 |

Example 3

| Feedstock | | Synthesis gas | Synthesis gas + isopropanol | Nitrogen + isopropanol |
|---|---|---|---|---|
| Catalyst | | ZnO—containing Fe—catalyst | | |
| Temperature | (°C.) | 330 | 330 | 330 |
| Pressure | (bars) | 10 | 10 | 10 |
| CO + $H_2$ feedstock | (V/Vh) | 839 | 866 | — |
| $N_2$ feedstock | (V/Vh) | — | — | 850 |
| Alcohol (gas) feedstock | (V/Vh) | — | 288 | 289 |
| Yield | (g/$Nm^3$) | | | |
| Methane | (g/$Nm^3$) | 14.6 | 17.0 | — |
| Ethane | (g/$Nm^3$) | 2.9 | 6.8 | — |
| Ethylene | (g/$Nm^3$) | 12.6 | 9.3 | — |
| Propane | (g/$Nm^3$) | 2.6 | 23.4 | 6.2 |
| Propylene | (g/$Nm^3$) | 18.8 | 35.3 | 7.0 |

-continued

| Feedstock | | Synthesis gas | Synthesis gas + isopropanol | Nitrogen + isopropanol |
|---|---|---|---|---|
| Butane | (g/Nm³) | 1.7 | 1.6 | 0.5 |
| Butene | (g/Nm³) | 13.1 | 11.8 | 3.1 |
| C₂–C₄ olefins | (g/Nm³) | 44.5 | 56.4 | 10.1 |

| Feedstock | | Synthesis gas | Synthesis gas + methanol | | | Nitrogen + methanol |
|---|---|---|---|---|---|---|
| Catalyst | | MgO—containing Fe—cataltst | | | | |
| Temperature | (°C.) | 340 | 340 | 340 | 340 | 340 |
| Pressure | (bars) | 10 | 10 | 10 | 12 | 12.9–14.9 |
| CO + H₂ feedstock | (V/Vh) | 1073 | 1040 | 1068 | 983 | — |
| N₂ feedstock | (V/Vh) | — | — | — | — | approx. 1000 |
| Alcohol (gas) feedstock | (V/Vh) | — | 227 | 585 | 1229 | 603 |
| Yield | (g/Nm³) | | | | | |
| Methane | (g/Nm³) | 29.6 | 31.8 | 41.1 | 38.9 | 13.2 |
| Ethane | (g/Nm³) | 8.1 | 8.0 | 8.0 | 7.6 | 1.6 |
| Ethylene | (g/Nm³) | 14.4 | 18.0 | 23.3 | 24.9 | 6.5 |
| Propane | (g/Nm³) | 5.8 | ~11.6 | 7.4 | 14.3 | 1.2 |
| Propylene | (g/Nm³) | 25.0 | 31.1 | 37.1 | 34.5 | 7.8 |
| Butane | (g/Nm³) | 2.8 | 3.4 | 5.4 | 4.8 | 0.8 |
| Butene | (g/Nm³) | 14.1 | 18.9 | 25.1 | 25.8 | 5.7 |
| C₂–C₄ olefins | (g/Nm³) | 53.5 | 68.0 | 85.5 | 85.2 | 20.0 |

While only a limited number of specific embodiments of the present invention have been expressly disclosed, it is, nonetheless, to be broadly construed and not to be limited except by the character of the claims appended hereto.

What we claim is:

1. In a process for the preparation of unsaturated hydrocarbons comprising catalytically hydrogenating carbon oxides with hydrogen at temperatures from 220° C. to 500° C. at pressures of up to 30 bars, in the presence of a catalyst having at least one group VIII metal selected from iron and cobalt and containing at least one difficulty reducible oxide from the group consisting of vanadium, manganese, titanium and thorium, the improvement which comprises carrying out said hydrogenating in the presence of at least one aliphatic alcohol having one to three carbon atoms, said alcohol being present in the vapor state.

2. The process of claim 1 wherein said catalytic hydrogenation takes place at 250° to 500° C.

3. The process of claim 1 wherein said hydrocarbons are olefins having 2 to 4 carbon atoms.

4. The process of claim 1 wherein the ratio of said carbon oxides and hydrogen to said alcohol in its vapor state is 1 to 4:1 by volume.

5. The process of claim 3 wherein the ratio of said carbon oxides and hydrogen to said alcohol in its vapor state is 1 to 4:1 by volume.

6. The process of claim 1 wherein said catalyst further comprises oxides of metals of Groups IIa and/or IIb of the Periodic Table.

7. The process of claim 3 wherein said catalyst further comprises oxides of metals of Groups IIa and/or IIb of the Periodic Table.

8. The process of claim 1 wherein the mole ratio of said carbon oxides to said hydrogen is 30:70 to 70:30.

9. The process of claim 3 wherein the mole ratio of said carbon oxides to said hydrogen is 30:70 to 70:30.

* * * * *